United States Patent

Mais et al.

[11] Patent Number: 6,150,571
[45] Date of Patent: Nov. 21, 2000

[54] PROCESS FOR THE PREPARATION OF 2,4-DICHLORO-3,5-DIMETHYL-FLUOROBENZENE

[75] Inventors: Franz-Josef Mais, Düsseldorf; Robert Horst Bloodworth, Köln; Karsten Von Dem Bruch, Leverkusen, all of Germany

[73] Assignee: Bayer Aktiengesellschaft, Leverkusen, Germany

[21] Appl. No.: 09/262,757

[22] Filed: Mar. 4, 1999

[30] Foreign Application Priority Data

Mar. 11, 1998 [DE] Germany .............................. 198 10 392

[51] Int. Cl.[7] .............................. C07C 19/08; C07C 22/00
[52] U.S. Cl. .............................................. 570/127; 570/143
[58] Field of Search ...................................... 570/143, 127

[56] References Cited

U.S. PATENT DOCUMENTS 4,925,994  5/1990  Mais et al. .
5,475,164  12/1995  Bussmann .
5,684,217  11/1997  Mais et al. .

FOREIGN PATENT DOCUMENTS 19717231  10/1998  Germany .

*Primary Examiner*—Alan Siegel
*Attorney, Agent, or Firm*—Joseph C. Gil; Diderico van Eyl

[57] ABSTRACT

A method for preparing 2,4-Dichloro-3,5-dimethylfluorobenzene, wherein the 2,4-Dichloro-3,5-dimethylfluorobenzene can be prepared in highisomeric selectivities when 3,5-dimethylfluorobenzene is chlorinated in the presence of Friedel-Crafts catalysts and a sulfur-containing co-catalyst.

The invention is also directed to an intermediary for preparing a pharmaceutically-active compound including 4-dichloro-3,5-dimethyl fluorobenzene.

11 Claims, No Drawings

PROCESS FOR THE PREPARATION OF 2,4-DICHLORO-3,5-DIMETHYL-FLUOROBENZENE

FIELD OF THE INVENTION

The present invention relates to a process for the preparation of 2,4-dichloro-3,5-dimethylfluorobenzene by selective chlorination of 3,5-dimethylfluorobenzene in the presence of specific catalysts.

BACKGROUND OF THE INVENTION 2,4-Dichloro-3,5-dimethylfluorobenzene is an intermediate for the preparation of pharmaceutically active compounds of the quinolone carboxylic acid type (see the applicant's earlier German Patent Application No. 197 17 231.8). The preparation of 2,4-dichloro-3,5-dimethylfluorobenzene, however, is not known from the prior art. The applicant's earlier patent application which has been mentioned above describes the preparation of 2,4-dichloro-3,5-dimethylfluorobenzene without the use of co-catalysts.

SUMMARY OF THE INVENTION

The invention relates to a process for preparing 2,4-dichloro-3,5-dimethylfluorobenzene which involves chlorinating 3,5-dimethylfluorobenzene in the presence of Friedel-Crafts catalysts and a sulfur-containing co-catalyst. The invention is also directed to the 2,4-dichloro-3,5-dimethylfluorobenzene.

DETAILED DESCRIPTION OF THE INVENTION 3,5-Dimethylfluorobenzene is commercially available.

Friedel-Crafts catalysts for the process according to the invention are known as such. Examples are: antimony chlorides, antimony oxychloride, aluminum chloride, iron(II)chloride, iron(III)chloride, tellurium chlorides, lead chlorides, molybdenum chlorides, tin chlorides, tungsten chlorides, titanium chlorides, zinc chlorides, boron trichloride and boron trifluoride. Elements and compounds of elements which, during chlorination, form a Friedel-Crafts catalyst (=Lewis acid) may also be employed (precursors of Friedel-Crafts catalysts). Examples of suitable Friedel-Crafts catalysts include the metals or semi-metals antimony, iron, lead, tin, zinc, molybdenum, tellurium or aluminum or their oxides, sulfides, carbonyls or salts (for example, carbonates). More specifically, examples of suitable compounds of elements include antimony oxides, iron oxides, iron sulfides, lead sulfides, tin sulfides, zinc sulfides, iron carbonyls, molybdenum carbonyls and boron phosphate. The corresponding fluorides, bromides and, if appropriate, iodides of the above-mentioned elements may also be employed in place of the chlorides mentioned. The following are preferably employed in the process according to the invention: antimony chlorides, iron, iron oxides, iron sulfides, iron carbonyls and iron(III)chloride. Iron(III) chloride is especially preferred. Friedel-Crafts catalysts and/or their precursors may be employed singly or as mixtures with each other.

The amount of the Friedel-Crafts catalyst or the precursors thereof may be varied within wide limits. For example, the addition of 0.0005% by weight frequently already results in a noticeable catalyst effect. On the other hand, it is also possible to add 5% by weight or more of the Friedel-Crafts catalyst; however, such high amounts are generally not advantageous but may entail disadvantages during work-up. The Friedel-Crafts catalyst is normally employed in an amount of 0.001 to 1.0% by weight, preferably 0.01 to 0.5% by weight. All these quantities are based on the amount of the 3,5-dimethylfluorobenzene employed.

Sulfur-containing co-catalysts for the process according to the invention which can be employed are elemental sulfur in its various forms or sulfur halides, for example, sulfur dichloride, sulfur tetrachloride, disulfur dichloride or disulfur dibromide.

Other co-catalysts which may be employed are, for example, heterocycles which simultaneously comprise N and S atoms and which belong, for example, to the thiazines, thiazepines, thiazocines, phenoxythines or thianthrenes. The following may be mentioned by way of example:

Thiazepines of the formulae

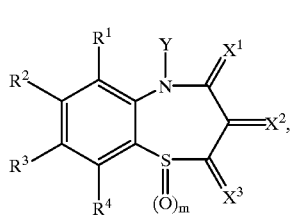

(I)

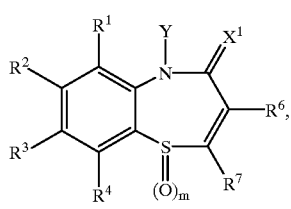

(II)

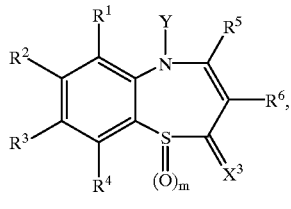

(III)

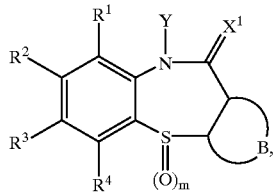

(IV)

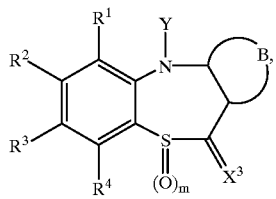

(V)

-continued

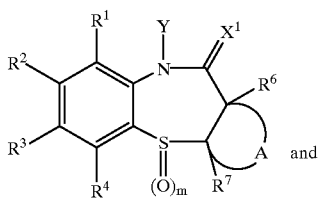

and

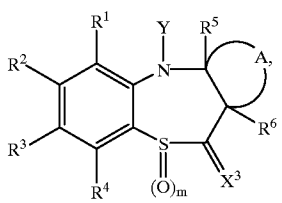

in which
R¹, R², R³, R⁴ are identical or different and represent hydrogen, hydroxyl, amino, cyano, halogen, nitro, nitroso, sulfonyl, sulfoxyl, tosyl, mercapto, carboxyl, carboxyarnide, carbalkoxy, dithiocarboxyl, thiocarboxyamide, dithiocarbalkoxy, optionally substituted alkyl, aryl, heteroaryl, alkoxy, aryloxy, heteroaryloxy, acyloxy, alkylthio, arylthio, heteroarylthio, acylthio, acyl, thioacyl or acylamino and which can furthermore with each other form one or more saturated or unsaturated, optionally substituted isocyclic or heterocyclic carbon rings having up to 8 C atoms, Y represents hydrogen, optionally substituted alkyl, aryl, heteroaryl, acyl, thioacyl, acyloxy, arylamino or acylamino, X¹, X² and X³ independently of one another in each case denote one of the following groups:

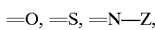

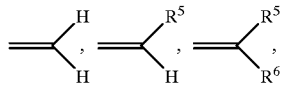

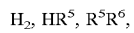

R⁵, R⁶ and R⁷ are identical or different and are as defined for R¹ to R⁴ with the exception that they cannot form rings with each other, Z is as defined for Y with the exception that Z cannot equal H, A represents the fusion of an optionally substituted saturated isocyclic or heterocyclic ring having up to 8 C atoms, B represents the fusion of an optionally substituted unsaturated isocyclic or heterocyclic ring having up to 8 C atoms and m is zero or 1.

Cyclic benzo-fused imines of the formula

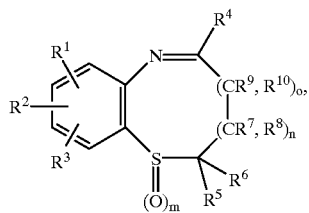

in which
R¹ and R² independently of one another represent hydrogen, hydroxyl, amino, cyano, halogen, nitro, carboxyl, halogenocarbonyl, carboxyamide, alkoxycarbonyl, alkyl, aryl, alkoxy, aryloxy, acyloxy, alkylthio, arylthio, acylthio, acyl, thioacyl or acylamino, R³ represents hydrogen or chlorine and furthermore together with one of the radicals R¹ or R² in the case of adjacent substitution and together with the substituted C atoms can form a fused saturated, unsaturated or aromatic isocyclic or heterocyclic ring having 5 to 8 ring atoms, R⁴ represents hydrogen, alkyl, aryl, halogen, alkylthio, arylthio, alkoxy, aryloxy, amino, hydrazino, alkylhydrazino or phenylhydrazino, m, n and o independently of one another can assume the value zero or 1, R⁵, R⁷ and R⁹ independently of one another represent hydrogen, alkyl, alkoxy, phenyl, acyloxy, cyano, halogen, carboxyl, alkoxycarbonyl, phenoxy or acyl, where R⁵ and R⁷ or R⁷ and R⁹ together with the substituted C atoms can form a saturated, unsaturated or aromatic isocyclic or heterocyclic ring having 5 to 8 ring atoms, R⁶, R⁸ and R¹⁰ independently of one another represent hydrogen, alkyl or halogen, where R⁶ and R⁸ or R⁸ and R¹⁰ together may form a double bond and where furthermore R⁵ and R⁶ together may represent divalent oxygen, sulfur or R¹¹-substituted nitrogen, R¹¹ representing alkyl, aryl, acyl, alkylamino or arylamino.

Benzo[f]-1,4-thiazepines of the formula

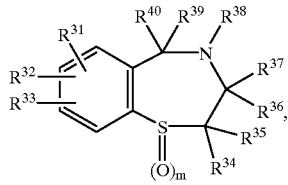

in which
R³¹ and R³² independently of one another represent hydrogen, hydroxyl, amino, cyano, halogen, nitro, $C_1-C_8$-alkyl, phenyl which is unsubstituted or substituted by R³¹ and R³² (with the exception of resubstitution by R³¹- and R³²-substituted phenyl), $C_1-C_8$-alkoxy, phenoxy, $C_1-C_8$-acyloxy, $C_1-C_8$-acyl or $C_1-C_8$-alkoxycarbonyl, R³³ represents hydrogen or chlorine and furthermore with one of the radicals R³¹ or R³² and together with the substituted C atoms can form a fused saturated, unsaturated or aromatic isocyclic or heterocyclic ring having 5 to 8 ring atoms, $R^{34}$, $R^{36}$ and $R^{40}$ independently of one another are hydrogen, $C_1$–$C_8$-alkyl, phenyl which is unsubstituted or substituted by $R^{31}$ and $R^{32}$ (with the exception of resubstitution by $R^{31}$- and $R^{32}$-substituted phenyl), $C_1$–$C_8$-acyl, $C_1$–$C_8$-alkoxycarbonyl, cyano, halogen, carboxyl, $C_1$–$C_8$-alkoxy, $C_1$–$C_8$-alkylthio, phenylthio, benzylthio, phenoxy or $C_1$–$C_8$-acyloxy, $R^{35}$, $R^{37}$ and $R^{39}$ independently of one another represent hydrogen, $C_1$–$C_8$-alkyl, halogen, $C_1$–$C_8$-alkoxy or $C_1$–$C_8$-alkylthio, $R^{38}$ represents hydrogen, $C_1$–$C_8$-alkyl, phenyl which is unsubstituted or substituted by $R^{31}$ and $R^{32}$ (with the exception of resubstitution by $R^{31}$- and $R^{32}$-substituted phenyl), $C_1$–$C_8$-acyl, $C_1$–$C_8$-thioacyl, halogenocarbonyl or $C_1$–$C_8$-alkoxycarbonyl and p is one of the numbers zero or 1, where furthermore the pair of substitutents $R^{34}$ and $R^{35}$, $R^{36}$ and $R^{37}$ and also $R^{39}$ and $R^{40}$ independently of one another can represent divalent oxygen, sulfur or $R^{38}$-substituted nitrogen and where furthermore the pair of substituents $R^{35}$ and $R^{36}$ and also $R^{38}$ and $R^{39}$ independently of one another can form a double bond, and where furthermore, the pair of substituents $R^{34}$ and $R^{37}$ and also $R^{38}$ and $R^{39}$ independently of one another can form 3- to 5-membered alkylene in which 1 or 2 C atoms can be replaced by oxygen, sulfur or $R^{38}$-substituted nitrogen, and where furthermore $R^{40}$ can also denote hydrazino, $C_1$–$C_8$-alkyl-hydrazino or phenyl-hydrazino.

Cyclic amidines which are oxy-substituted on the exocyclic N atom of the formula

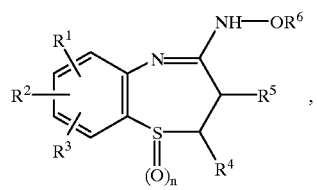

(X)

in which $R^1$ and $R^2$ independently of one another represent hydrogen, cyano, halogen, carboxyl, alkoxycarbonyl, alkyl, aryl, alkoxy, aryloxy or acyl, $R^3$ represents hydrogen, alkyl or chlorine and furthermore with one of the radicals $R^1$ or $R^2$ in the case of adjacent substitution and together with the substituted C atoms can form a fused saturated, unsaturated or aromatic, isocyclic or heterocyclic ring having 5 to 8 ring atoms, $R^4$ and $R^5$ independently of one another represent hydrogen, alkyl, aryl, halogen, alkoxy, aryloxy, acyl or acyloxy or together with the substituted C atoms can form a saturated or unsaturated, isocyclic or heterocyclic ring having 5 to 8 ring atoms, $R^6$ represents hydrogen, alkyl, aryl or silyl which is substituted by alkyl or aryl and n can denote the value zero or 1.

1,6-Benzo-thiazocines of the formula

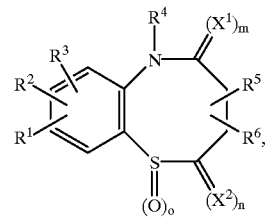

(XI)

in which $R^1$ and $R^2$ independently of one another represent hydrogen, hydroxyl, amino, cyano, halogen, nitro, alkylsulfonyl, phenylsulfonyl, alkylsulfoxyl, phenylsulfoxyl, tosyl, mercapto, carboxyl, halogenocarbonyl, carboxyamide, alkoxycarbonyl, thiocarboxyamide, alkyl, aryl, heteroaryl, alkoxy, aryloxy, heteroaryloxy, acyloxy, alkylthio, arylthio, heteroarylthio, acylthio, acyl, thioacyl or acylamino, $R^3$ represents hydrogen or chlorine, and furthermore with one of the radicals $R^1$ or $R^2$ and together with the substituted C atoms, can form a fused saturated, unsaturated or aromatic isocyclic or heterocyclic ring having 5 to 8 ring atoms, $R^4$ represents hydrogen, alkyl, aryl, heteroaryl, acyl, thioacyl, halogenocarbonyl or alkoxycarbonyl, $X^1$ and $X^2$ independently of one another represent divalent oxygen, sulfur or $R^7$-substituted nitrogen, where the meaning of $R^7$ extends to the scope of $R^4$ with the exception of hydrogen, m, n and o independently of one another can in each case denote the value zero or 1 and $R^5$ and $R^6$ independently of one another can be attached to one or to two of the C atoms located between the S and the N atom in the 8-membered ring as long as these C atoms are not occupied by $X^1/X^2$ and their meaning extends to the scope of $R^1/R^2$, in the case of adjacent substitution it also being possible to form, with the substituted C atoms, a saturated, unsaturated or aromatic isocyclic or heterocyclic ring having 5 to 8 ring atoms and it furthermore being possible for $R^5$ and $R^6$ together to denote divalent oxygen or sulfur.

N-substituted phenothiazine derivatives of the formula

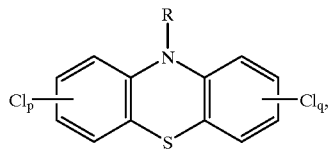

(XII)

in which

R is an aryl radical or

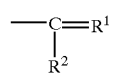

where $R^1$ represents oxygen, sulfur, $H_2$ or $X_2$ and X is Br or Cl and

R² represents an aryl radical, Br, Cl or the radical —CH$_x$X$_y$
in which
X is Br or Cl and
x is a value from 1 to 3 and
x+y=3 or
in which
R is a CF$_3$—(CF$_2$)$_n$—CO— radical in which n represents zero, 1, 2 or 3 or
in which
R is a —CO—O—aryl where aryl=phenyl or optionally substituted phenyl and p+q always equals an integer from zero to 4.

Other co-catalysts which can be employed for the process according to the invention are heterocycles which comprise only sulfur as hetero atoms or which simultaneously comprise O and S atoms and which belong, for example, to the classes of the thianthrenes or phenoxathiines. For example, such compounds have the formula

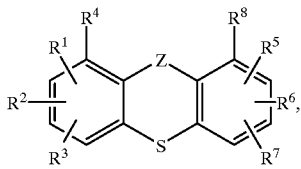

(XIII)

in which Z represents —O— or —S—
and
R$^1$ to R$^8$ independently of one another represent hydrogen, fluorine, chlorine, bromine, nitro, C$_1$–C$_4$-alkyl, C$_1$–C$_4$-acyl, C$_1$–C4-alkoxy, C$_1$–C$_4$-acyloxy, aryl or cyano.

Unless otherwise specified, the substituents in formulae (I) to (XIII) can have the following meanings: alkyl groups, aryl groups, acyl groups, halogen groups, and hetaryl and heterocyclic rings. Suitable alkyl groups include composite groups such as alkoxy, alkylthio, alkylamino, alkylsulfonyl, alkylhydrazino, carbalkoxy, dithiocarbalkoxy and alkoxycarbonyl is, more specifically C$_1$–C$_8$-alkyl groups, in particular C$_1$–C$_4$-alkyl. Examples of suitable aryl groups include composite groups such as aryloxy, arylthio and arylamino, is, for example, C$_6$–C$_{10}$-aryl, in particular phenyl. Examples of suitable acyl groups include composite groups such as acyloxy, acylthio, thioacyl and acylamino is, e.g., C$_1$–C$_6$-acyl groups, in particular C$_1$–C$_3$-acyl. Examples of suitable halogen groups include composite groups such as halogenocarbonyl, e.g., fluorine, chlorine or bromine, in particular fluorine or chlorine. Examples of suitable hetaryl and heterocyclic rings include composite groups such as hetaryloxy and hetarylthio, e.g., aromatic rings which have 1 to 3 hetero atoms selected from the group consisting of oxygen, sulfur and nitrogen atoms in the ring and a total of 6 to 10 ring atoms.

1,4-Thiazepine derivatives, N-acylated phenothiazines, halogen- or alkyl-substituted thianthrenes or phenoxathiines and also sulfur or sulfur halides are preferably employed. It is furthermore possible to employ, in the process according to the invention, the co-catalysts in combination with other elements or compounds which have not been described as co-catalysts. The co-catalysts can be employed both singly and as a mixture of a plurality thereof. The amounts in which co-catalysts can be employed can vary within wide limits. Amounts of less than 0.001% by weight are less advantageous since the effect as co-catalyst is less pronounced. It is even possible to employ amounts of 5% by weight or more of co-catalyst, however, these high amounts are generally of no advantage but may cause disadvantages during work-up. Thus, the co-catalysts to be used according to the invention can be employed in an amount of 0.001–1.0% by weight, preferably 0.001–0.5% by weight, especially preferably 0.005–0.1% by weight, in each case based on 3,5-dimethylfluorobenzene employed.

The molar ratio of Friedel-Crafts catalyst(s) or precursors thereof and co-catalyst(s) in the process according to the invention may be varied within wide limits. An example of a suitable molar ratio of Friedel-Crafts catalyst or precursors thereof to co-catalyst is from 100:1 to 1:100, preferably 75:1 to 1:50 and especially preferably 50:1 to 1:10.

The process according to the invention is expediently carried out in the liquid phase. If appropriate, inert solvents may be used as diluents. Suitable solvents are those which are not attacked by chlorine under the conditions of a chlorination in the nucleus and which are known to those skilled in the art for this purpose, such as methylene chloride, chloroform, carbon tetrachloride and acetic acid. It is preferred to carry out the process without solvent.

Examples of chlorinating agents which can be used in the process according to the invention are chlorine or substances which liberate chlorine under the reaction conditions, such as sulfuryl chloride. Chlorine is preferred and may be passed into the reaction mixture in liquid or gaseous form. It is preferred to employ gaseous chlorine.

The amount of chlorinating agent is preferably chosen in such a way that a degree of chlorination of not substantially greater than 2 results. Higher degrees of chlorination are possible but not advantageous since they lead to the formation of 2,4,6-trichloro-3,5-dimethylfluorobenzene. On the other hand, it may be advantageous to meter in markedly less than 2 moles of chlorinating agent per mole of 3,5-dimethylfluorobenzene to avoid almost completely formation of the trichlorinated product. The chlorinating agent is therefore employed for example in an amount of 1.0 to 2.2 moles, preferably 1.25 to 2.1 moles, especially preferably 1.5 to 2.0 moles per mole of 3,5-dimethylfluorobenzene.

The chlorination in the nucleus which is to be carried out according to the invention can be carried out, in principle, at a temperature ranging from the solidification point up to the boiling point of the reaction mixture. In general, the reaction temperature is from 0 to 120° C., preferably 20 to 100° C., especially preferably 30 to 90° C. The temperature within the limits indicated is chosen in the course of the process in such a way that the chlorination mixture always remains liquid, or virtually liquid.

The reaction pressure can be atmospheric, sub-atmospheric or super-atmospheric and is, in principle, not critical. Atmospheric pressure is preferred for economic reasons. Super-atmospheric pressure may be indicated for example when the process is to be carried out above the boiling point of a low-boiling solvent. In this case, the reaction may be carried out, for example, under the inherent pressure of the reaction mixture which it establishes.

The water content of the reaction mixture is generally not critical. It is preferred not specifically to dry all starting materials but to employ them at the (low) water content at which they are normally present in chemical technology. however, it is also possible specifically to dry individual or all substances of the reaction mixture. The water content of the starting materials should normally not exceed the saturation limits of the starting materials in question. Preferred according to the invention are water contents in the chlorination mixture of less than 250 ppm, more preferably less than 150 ppm, and even more preferably less than 100 ppm.

To carry out the process according to the invention in practice, the sequence in which the individual components are added to the reaction mixture is as desired. The process may be carried out continuously or batchwise. For example, 3,5-dimethylfluorobenzene is introduced into the reaction vessel at the desired reaction temperature, Friedel-Crafts catalyst and sulfur-containing co-catalyst are added, and the chlorinating agent is metered in up to the desired degree of chlorination.

If the chlorination process is carried out without solvent, it is possible that solids precipitate from the chlorination mixture at relatively low temperatures, e.g., below 45° C., starting from the point at which, for example, 1.6 moles of chlorinating agent are added per mole of 3,5-dimethylfluorobenzene. If it is desired to continue with the chlorination in such cases, the mixture can be kept virtually completely liquid by raising the temperature to, for example, at least 75° C.

The reaction mixture is subsequently worked up, for example, by distillation. The 4-chloro-3,5-dimethylfluorobenzene which is also present in the chlorination mixture can be separated by distillation and returned to the next chlorination according to the invention. Then, the 2,4-dichloro-3,5-dimethylfluorobenzene fraction can be separated off. The isomeric selectivity in the process according to the invention is so high that this fraction generally contains, inter alia, well above 98% by weight of the desired 2,4-dichloro-3,5-dimethylfluorobenzene.

The 2,4-Dichloro-3,5-dimethylfluorobenzene can be used as an intermediate for the preparation of pharmaceutically active compounds of the quinolone carboxylic acid type.

The examples which follow are intended to illustrate the process according to the invention without imposing any limitations.

EXAMPLES

Example 1

124.0 g of 3,5-dimethylfluorobenzene, 0.12 g of FeCl$_3$ and 0.05 g of N-trifluoroacetylphenothiazine were introduced into a chlorinating vessel at 40° C., and 107 g of chlorine gas were passed in over 6 hours at a uniform rate. The resulting product mixture was analyzed by GC. It contained 44.80% of 4-chloro-3,5-dimethylfluorobenzene, 53.76% of 2,4-dichloro-3,5-dimethylfluorobenzene, 0.95% of 2,6-dichloro-3,5-dimethyl-fluorobenzene and 0.14% of 2,4,6-trichloro-3,5-dimethylfluorobenzene (remainder: unidentified products). The formation selectivity for the total of 4-chloro-3,5-dimethylfluorobenzene and 2,4-dichloro-3,5-dimethyl-fluorobenzene was therefore 98.56%.

Example 2

124.0 g of 3,5-dimethylfluorobenzene, 0.25 of FeCl$_3$ and 0.054 g of co-catalyst of the formula

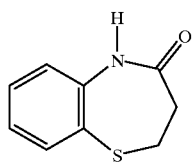

were introduced into a chlorinating vessel. 113 g of chlorine were introduced at 40° C., and then a further 30 g of chlorine at 40 rising to 77° C. (total chlorinating time 5 hours). The product obtained was analyzed by GC. It contained 1.21% of 4-chloro-3,5-dimethylfluorobenzene, 94.47% of 2,4-dichloro-3,5-dimethylfluorobenzene, 0.24% of 2,6-dichloro-3,5-dimethylfluorobenzene and 3.85% of 2,4,6-trichloro-3,5-dimethyl-fluorobenzene (remainder: unidentified products). The calculated isomeric purity of the dichlorinated fraction was thus 99.75%.

Example 3

The process of Example 2 was repeated, but 0.059 g of the compound of the formula

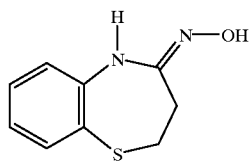

was employed as the co-catalyst. 110 g of chlorine were passed in at 40° C. and then a further 15 g of chlorine and 40 to 60° C. (total chlorination time 5 hours). GC analysis of the chlorination mixture revealed the following composition: 18.98% of 4-chloro-3,5-dimethylfluorobenzene, 79.99% of 2,4-dichloro-3,5-dimethylfluorobenzene, 0.76% of 2,6-dichloro-3,5-dimethylfluorobenzene and 0.17% of 2,4,6-trichloro-3,5-dimethylfluoro-benzene (remainder: unidentified products).

Example 4

124.0 g of 3,5-dimethylfluorobenzene, 0.24 g of FeCl$_3$ and 0.82 g of sulfur were introduced into a chlorinating vessel. 119 g of chlorine were passed in at 40° C. and then a further 5 g of chlorine at 40–58° C. (chlorination time 5 hours). GC analysis revealed the following composition: 24.67% of 4-chloro-3,5-dimethylfluorobenzene, 73.34% of 2,4-dichloro-3,5-dimethylfluorobenzene, 0.38% of 2,6-dichloro-3,5-dimethylfluorobenzene and 0.52% of 2,4,6-trichloro-3,5-dimethylfluorobenzene (remainder: unidentified products). The formation selectivity for the total of 4-chloro-3,5-dimethylfluorobenzene and 2,4-dichloro-3,5-dimethylfluorobenzene was therefore 98.01%.

Example 5

The process of Example 4 was repeated, but only 0.12 g of FeCl$_3$ was employed and 0.09 g of disulfur dichloride was employed instead of sulfur. 106 g of chlorine were passed in at 40° C. and a further 36 g of chlorine at 40 to 79° C. (chlorination time 5 hours). GC analysis revealed the following composition of the chlorination mixture: 2.10% of 4-chloro-3,5-dimethylfluorobenzene, 93.81% of 2,4-dichloro-3,5-dimethyl-fluorobenzene, 0.17% of 2,6-dichloro-3,5-dimethylfluorobenzene and 2.56% of 2,4,6-trichloro-3,5-dimethylfluorobenzene (remainder: unidentified products). The calculated isomeric purity of the dichlorinated fraction was thus 99.8%.

Example 6

124.0 g of 3,5-dimethylfluorobenzene, 0.3 g of FeCl$_3$ and 0.4 g of co-catalyst of the formula

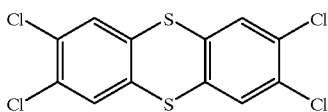

were introduced into a chlorinating vessel at 60° C. 120 g of chlorine were passed in at this temperature in the course of 8 hours at a uniform rate. GC analysis of the chlorination mixture revealed: 21.09% of 4-chloro-3,5-dimethylfluorobenzene, 77.23% of 2,4-dichloro-3,5-dimethylfluorobenzene, 1.13% of 2,6-dichloro-3,5-dimethylfluorobenzene and 0.31% of 2,4,6-trichloro-3,5-dimethylfluorobenzene (remainder: unidentified products).

Example 7

The process of Example 6 was repeated, but the co-catalyst used was 0.4 g of compounds of the formula

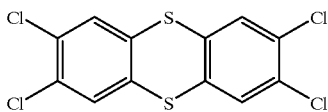

in the form of an isomer mixture obtained by chlorinating

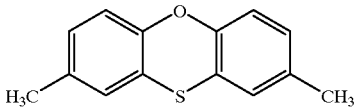

with 4 moles of $Cl_2$ (see EP-A 173 222).

GC analysis of the chlorination mixture revealed the following composition: 20.55% of 4-chloro-3,5-dimethylfluorobenzene, 77.50% of 2,4-dichloro-3,5-dimethylfluorobenzene, 1.07% of 2,6-dichloro-3,5-dimethylfluorobenzene and 0.48% of 2,4,6-trichloro-3,5-dimethylfluorobenzene (remainder: unidentified products).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing 2,4-dichloro-3,5-dimethylfluorobenzene, comprising chlorinating 3,5-dimethylfluorobenzene in the presence of Friedel-Crafts catalysts and a sulfur-containing co-catalyst.

2. The process of claim 1, wherein the Friedel-Crafts catalysts used comprise a catalyst component selected from the group consisting of antimony chlorides, antimony oxychloride, aluminum chloride, iron(II)chloride, iron(III) chloride, tellurium chlorides, lead chlorides, molybdenum chlorides, tin chlorides, tungsten chlorides, titanium chlorides, zinc chlorides, boron trichloride, boron trifluoride, and elements and compounds of elements which, during chlorination, form a Friedel-Crafts catalyst.

3. The process of claim 1, wherein the catalyst component is used in an amount ranging from 0.0005 to 5% by weight of Friedel-Crafts catalyst, based on the amount of 3,5-dimethylfluorobenzene employed.

4. The process of claim 1, wherein the sulfur-containing co-catalysts employed comprises a catalyst component selected from the group consisting of sulfur, sulfur halides or heterocycles which simultaneously comprise N and S atoms.

5. The process of claim 1, wherein the co-catalysts employed are heterocycles of the classes of the thiazines, thiazepines, thiazocines, phenoxathiines and thianthrenes.

6. The process of claim 1, wherein the co-catalysts are employed in amounts of 0.001 to 5% by weight, based on 3,5-dimethylfluorobenzene employed.

7. The process of claim 1, wherein the molar ratio of Friedel-Crafts catalyst or precursors thereof to co-catalyst is 100:1 to 1:100.

8. The process of claim 1, wherein the chlorinating agent employed is chlorine or a substance which liberates chlorine under the reaction conditions, in an amount of 1.0 to 2.2 moles per mole of 3,5-dimethylfluorobenzene.

9. The process of claim 1, wherein the process occurs at a reaction temperature ranging from 0 to 120° C., atmospheric pressure, and wherein the temperature, wherein the chlorination mixture remains liquid or virtually liquid.

10. The 2,4-dichloro-3,5-dimethvifluorobenzene of claim 1.

11. An intermediary comprising 2,4-dichloro-3,5-dimethylfluorobenzene.

* * * * *